United States Patent [19]

Kita et al.

[11] Patent Number: 5,041,283

[45] Date of Patent: Aug. 20, 1991

[54] COSMETIC COMPOSITION

[75] Inventors: Katsumi Kita, Izumisano; Tetsuo Uno, Wakayama; Shinichi Masuda, Utsunomiya; Kazuyuki Yahagi, Tokyo; Kazuhiro Tashiro, Funabashi, all of Japan

[73] Assignee: Kao Corporation, Tokyo, Japan

[21] Appl. No.: 404,409

[22] Filed: Sep. 8, 1989

[51] Int. Cl.⁵ ............................................. A61K 7/00
[52] U.S. Cl. .................................. 424/64; 424/63; 424/70; 424/72; 514/724; 514/738; 568/764; 568/853
[58] Field of Search .................. 424/64, 63, 70, 72; 514/724, 738; 568/764, 853

[56] References Cited

U.S. PATENT DOCUMENTS

| | | | |
|---|---|---|---|
| 2,292,926 | 8/1942 | Brubaker et al. | 568/853 |
| 2,400,724 | 5/1946 | Walker | 568/853 |
| 2,752,399 | 6/1956 | Grimme et al. | 568/853 |
| 2,991,297 | 7/1961 | Cooley et al. | 260/410.6 |
| 4,061,581 | 12/1977 | Leleu et al. | 260/410.6 |
| 4,122,290 | 10/1978 | Immel et al. | 568/853 |
| 4,655,947 | 4/1987 | Tsai et al. | 252/49.5 |

FOREIGN PATENT DOCUMENTS 0193837  11/1984  Japan ................................ 568/853

OTHER PUBLICATIONS

Patent Abstracts of Japan, vol. 14, No. 57 (C-684)[4000], Feb. 2, 1990; & JP-A-1 283 235 (Kao Corp.) 11-14-1989 *Abstract*.

*Primary Examiner*—Thurman Page
*Assistant Examiner*—James M. Spear
*Attorney, Agent, or Firm*—Oblon, Spivak, McClelland, Maier & Neustadt

[57] ABSTRACT

A cosmetic composition comprising a long-chain alkyltrimethylol is disclosed. The alkyltrimethylol is represented by the formula (I):

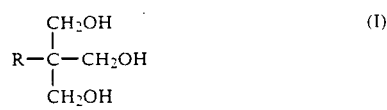

wherein R is a linear or branched, saturated or unsaturated alkyl group having 8-22 carbon atoms. The composition is applied to various types of cosmetic and exhibits superior extendibility when applied, imparts a non-sticky, fresh feeling upon use, and provides an excellent moisture-retaining effect.

6 Claims, 1 Drawing Sheet

COSMETIC COMPOSITION

BACKGROUND OF THE INVENTION

1. Field of the Invention

The present invention relates to a novel cosmetic composition, and, more particularly, to a cosmetic composition comprising a long-chain alkyltrimethylol which exhibits superior extendibility when applied, imparts a non-sticky, fresh feeling upon use, and provides an excellent moisture-retaining effect. The cosmetic composition possesses a good emulsion stability.

2. Description of the Background

Conventionally, various types of moisturizing agents have been used for cosmetic compositions. Such moisturizing agents do not exhibit sufficient effects if the amount formulated is small. If, on the other hand, a large amount is formulated, cosmetics tend to impart an unfavorable feeling to the skin or their stability tends to be impaired.

Emulsion type cosmetics are widely used owing to their capability of imparting both oil and water to skins and hairs. Various types of emulsion type cosmetics with varied characteristics and sensation upon use can be prepared by changing the types and amounts of oil components.

An emulsion, however, is a thermodynamically unstable system. Various attempts and studies have been undertaken to stabilize emulsion systems. One of the measures of the emulsion system stabilization is the use of emulsifying adjuvants. Such emulsifying adjuvants include cationic-, anionic-, amphoteric-, and nonionic type. Of these, nonionic type is preferable because of its broader spectrum of oil components which can be used together.

Higher alcohols such as cetanol and cetostearyl alcohol are known as examples of nonionic type emulsifying adjuvant. Addition of such a higher alcohol to a cosmetic emulsion produces a liquid crystal structure and this structure helps the emulsion to stabilize. The addition of a higher alcohol is effective from the aspect of preventing oils and fats having a high melting point from crystallizing. However, if a higher alcohol is added in an amount sufficient to maintain such oils and fats in a stable condition, viscosity of the cosmetic becomes so high that it cannot adequately extend on the skin when applied and imparts an excessive oily, sticky sensation. In addition, the liquid crystal structure produced by the use of a higher alcohol, when destroyed, deposits crystals having pearl-like gloss and lowers the viscosity of the composition.

In order to overcome such defects in liquid crystal structures, compositions to which a nonionic type emulsifying adjuvant capable of producing a lamella type liquid crystal structure have been developed. For example, Japanese Patent Publication No. 5050/1963 discloses a skin and hair protecting agent comprising a triol represented by the formula (II):

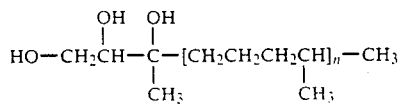

wherein n is an integer of 1-3.

The triol, however, has a defect of forming liquid crystals with a reversed middle structure in an aqueous solution which imparts an oily sensation and does not exhibit a sufficient moisture-retaining effect. Japanese Patent Laid-open No. 23737/1988 discloses an aqueous niosome dispersion comprising lipid lamella formed using polyglycerolether as a nonionic amphiphilic compound in an attempt to promote the stability by encapsulating water-soluble active components in an aqueous compartment which is encircled by lipid layers. Such an aqueous niosome dispersion, however, requires treatment at a high temperature of above 80° C. to produce a niosome encapsulating active components. This makes it difficult to apply the method to active components which are not stable at a high temperature. Japanese Patent Publication No. 8287/1983, Japanese Patent Publication No. 56016/1986, Japanese Patent Laid-open No. 77613/1982, and Japanese Patent Laid-open No. 94326/1982 disclose aqueous dispersions of lipid spheres by the use of polyglycerolether. Industrial production of aqueous dispersions of lipid spheres, however, involves difficulties such as requirement of a homogenizing procedure, use of organic solvents such as chloroform and methanol for dissolving lipids, complicated vaporization processes for removing the solvents, etc.

Nonionic emulsifying adjuvants conventionally used thus have drawbacks in that they have narrow concentration ranges for liquid crystal formation, require a high temperature for forming liquid crystals, and are difficult to produce liquid crystals industrially.

Cosmetic compositions in which high melting point active components are not uniformly dispersed or adequately emulsified do not exhibit a sufficient moisture-retaining effect. Although some nonionic emulsifying adjuvants can exhibit moisturizing effects such effects are not sufficient.

Accordingly, development of cosmetic compositions which do not cause crystal transformation and remain homogeneous with superior stability over a wide range of temperature at which they are used, and which do not impart oily sensation and exhibit an excellent moisturizing effect has been desired.

In view of this situation, the present inventors have conducted extensive studies to resolve the above-mentioned problems in conventional cosmetic compositions, and found that cosmetic compositions having an excellent moisturizing effect could be produced by the use of a certain type of long-chain alkyltrimethylol and that if such a long-chain alkyltrimethylol is formulated in emulsion type cosmetic compositions, in addition to the excellent moisturizing effect, further effects could be obtained such as stabilizing emulsions and broadening the range in which high boiling point active components are maintained homogeneous. The inventors have further found that the emulsion cosmetic compositions exhibited superior extendibility when applied and imparted a non-sticky, fresh feeling upon use. Such findings have led to the completion of the present invention.

SUMMARY OF THE INVENTION

Accordingly, an object of this invention is to provide a cosmetic composition comprising one or more long-chain alkyltrimethylols represented by the following formula (I)

wherein R represents a linear or branched, saturated or unsaturated alkyl group having 8-22 carbon atoms.

In a preferred embodiment said long-chain alkyltrimethylol is a branched alkyl type long-chain alkyltrimethylol represented by the following formula (III):

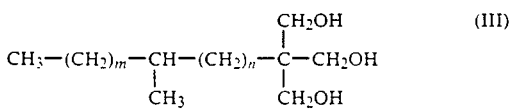

wherein m and n are independently an integer of 0–19, provided that the sum m+n is 7–19.

Since a branched alkyl type long-chain alkyltrimethylol of the formula (III) is a novel compound, it is another object of the present invention to provide such a novel compound.

Other objects, features and advantages of the invention will hereinafter become more readily apparent from the following description.

DETAILED DESCRIPTION OF THE INVENTION AND PREFERRED EMBODIMENTS

Figure 1:
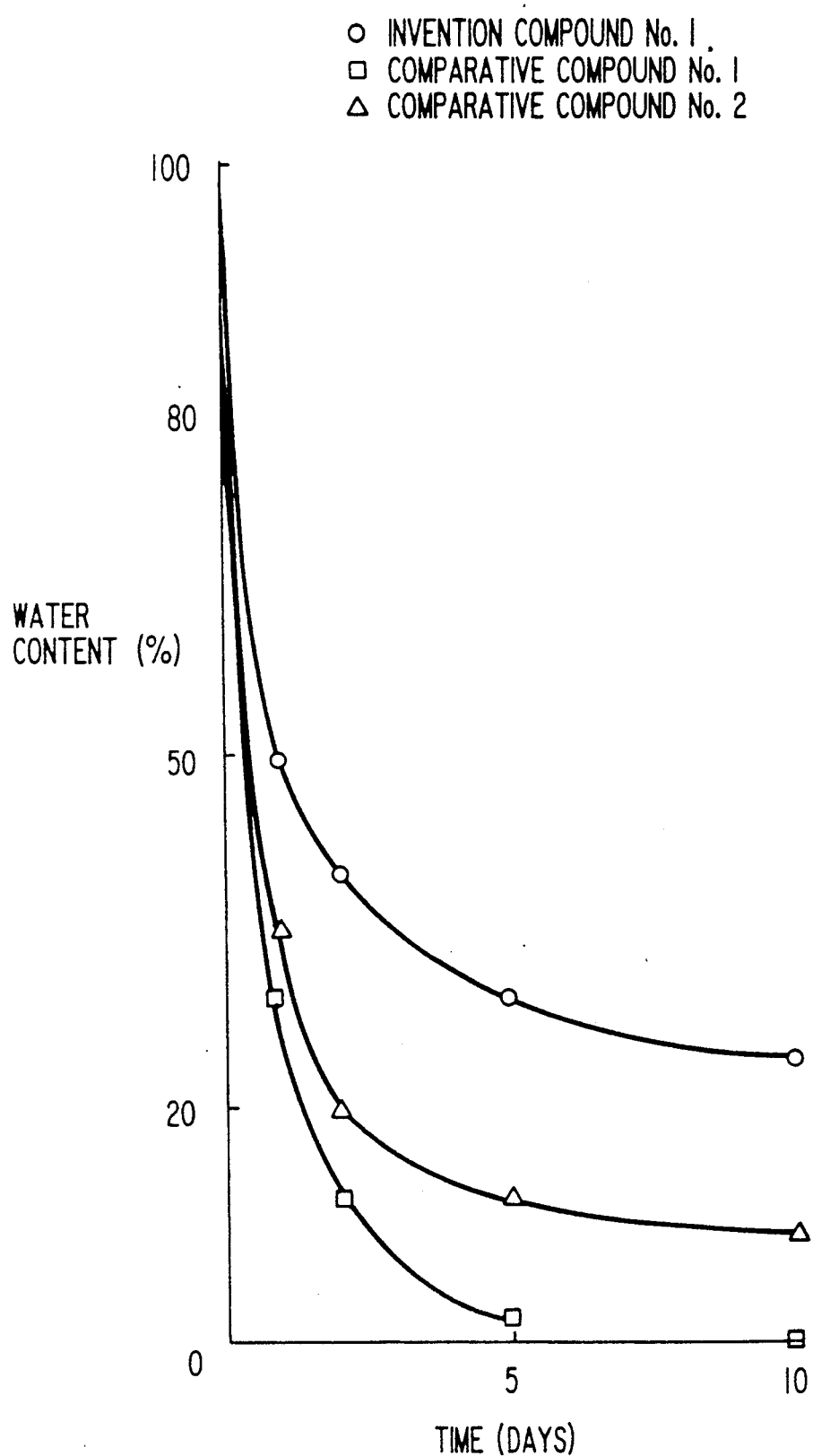
FIG. 1 is a drawing showing changes in water content over time of a compound of the present invention and comparative compounds.

Long-chained alkyltrimethylols which can be used in this invention are represented by the formula (I) and include trimethylolundecane, trimethyloltridecane, trimethylolpentadecane, trimethylolheptadecane, trimethylolnonadecane, trimethylolheneicosane, and the like. Among these, branched alkyl type long-chain alkyltrimethylols represented by the following formula (III) are preferable:

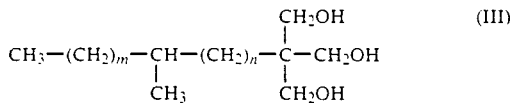

wherein m and n are independently an integer of 0–19, provided that the sum m+n is 7–19, with especially preferable range of the sum m+n being 11–15. The most preferable compound is trimethylolisoheptadecane having the value m+n of 13. These branched alkyl type long-chain alkyltrimethylols of the formula (III) are novel compounds. They are lamella-type liquid crystals at room temperature, possess superior dissolving ability with almost all solvents, and disperse uniformly in water.

A long-chain alkyltrimethylol can be prepared, for example, by reacting the corresponding aldehyde with formaldehyde in a suitable solvent in the presence of a base according to the following reaction scheme:

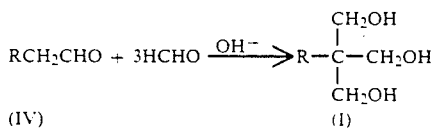

wherein R has the same meaning as defined above.

More specifically, as is well known, the reaction comprises a first, condensation reaction step in which 1 mole of aldehyde reacts with 2 moles of formaldehyde and a second, Cannizzaro reaction in which additional one mole of formaldehyde and a base react to produce a trimethylol.

Aldehyde (IV) used in the above reaction can be prepared by the catalytic reduction, using, for example, palladium carbon, of an acid chloride of the corresponding carboxylic acid [Synthesis, 767 (1976)]. Given as a typical carboxylic acid is methyl-branched carboxylic acids with carbon atom contents of about 18 and containing isostearic acid as a major carboxylic acid component, which is produced as a by-product in a process for the manufacture of oleic acid dimer [J. Amer. Oil Chem. Soc., Vol. 51, 522 (1974)].

Lower alcohols such as ethanol, isopropanol, etc., ethers such as tetrahydrofuran, dioxane, etc., hydrocarbons, and halogenated hydrocarbons are given as examples of organic solvents used in the above reaction. Among these, isopropanol, tetrahydrofuran, and dioxane are preferable. The amount of an organic solvent which is used is 20–1,000% by weight, and preferably 100–300% by weight, of the amount of aldehyde used. The solvent is usually charged into the reaction vessel in advance. Alternatively, it can be added to the reaction mixture during the reaction. A part of the organic solvent can be used mixed with water. The reaction may be carried out even without using an organic solvent.

Given as examples of bases which can be used in the reaction are hydroxides of alkali metal and alkali earth metal such as sodium hydroxide, potassium hydroxide, calcium hydroxide, etc., and sodium carbonate, calcium carbonate, and the like. Preferable bases are sodium hydroxide and potassium hydroxide. The amount of the base to be used is in a range of 1.1–3.5 mole equivalents, and preferably 1.5–2.0 mole equivalents, per one mole of aldehyde. The use of a base as an aqueous solution of a 50% or smaller concentration is desirable from the aspect of the process operation.

Formaldehyde can be used as is or as an aqueous solution. Use of paraformaldehyde is also acceptable. There are no specific limitations as to the concentration of formaldehyde when it is used as an aqueous solution. The use of a formaldehyde aqueous solution with 5–50% concentration which is readily available is advantageous. The amount of formaldehyde is 3–30 mole, and preferably 4–8 mole per mole of aldehyde.

There are no specific limitations as to order of the addition of aldehyde, formaldehyde, and base to the reaction system. A desirable result can be obtained when aldehyde and base are added dropwise simultaneously to a formaldehyde solution. The reaction temperature is usually 20–100° C., and preferably 30–60° C.

A long-chain alkyltrimethylol thus prepared can be used individually or two or more of long-chain alkyltrimethylols can be used together. There are no specific limitations as to the amount of a long-chain alkyltrimethylol to be formulated to the cosmetic composition of the present invention. Usually, an amount of 0.01–80% by weight is preferable, with an especially preferable amount being in the range of 0.1–50% by weight.

Surface active agents can be used to increase the effect of the present invention. Any surface active agents, including cationic-, anionic-, amphoteric-, and nonionic type, can be used. Nonionic surface active agents are preferable for skin cosmetic compositions, while cationic surface active agents are preferable for hair cosmetic compositions. Examples of nonionic surface active agents include polyoxyethylenealkyl ether, polyoxyethylenealkylphenyl ether, polyoxyethylene fatty acid ester, sorbitan fatty acid ester, polyoxyethylene sorbitan fatty acid ester, polyoxyethylene fatty acid monoglyceride, glycerine ether, and the like. Given as typical examples of cationic surface active agents are quaternary ammonium salts. Any quaternary ammonium salts which are commonly used for cosmetic compositions can be used for the purpose of the present invention. Preferable quaternary ammonium salts are a branched alkyl type which is described in Japanese Patent Laid-open No. 267505/1986. A surface active agent is formulated in an amount of 0.01-30% by weight, and preferably 0.1-10% by weight, in the cosmetic composition.

In addition to the above essential components, various types of ingredients which are commonly used for cosmetics, drugs, and foods can be optionally added to the cosmetic composition of the present invention. Such optional ingredients include higher alcohols having a linear or branched alkyl or alkenyl group, hydrocarbons such as liquid paraffin, petrolatum, solid paraffin, etc., lanolin derivatives such as liquid lanolin, lanolin fatty acid, etc., silicone derivatives such as dimethylpolysiloxanes, polyether-modified polysiloxanes, amino-modified polysiloxanes, etc., oils and fats such as higher fatty acid esters of higher alcohols, higher fatty acids, long-chain amidoamines having an alkyl or alkenyl group, etc., natural oils and fats of animal or vegetable origin such as mink oil, olive oil, etc., medicinal ingredients such as antidandruffs, antiseptics, vitamins, etc., preservatives such as paraben, etc., viscosity increasing agents such as water soluble polymeric compounds, etc., coloring agents such as dyes and pigments, UV absorbers, astringents, other types of moisture-retaining agents, including propylene glycol, glycerol, carbitol, 3-methyl-1,3-butanediol, sugars, etc., water, perfumes, and the like.

The cosmetic composition of the present invention can be prepared according to conventional methods. It can be applied to various types of cosmetics, for example, to basic cosmetics of oil-in-water-, water-in-oil-, or oil type, make-up cosmetics such as lip sticks, foundations, and the like, skin cleansers, hair cosmetics such as hair rinse, hair treatment agents, and the like.

In the cosmetic composition of the present invention a long-chain alkyltrimethylol provides a superior moisture-retaining effect. Since a long-chain alkyltrimethylol is capable of producing lamella type liquid crystals, the cosmetic composition exhibits superior extendibility when applied and imparts a non-sticky, fresh feeling upon use. In addition, since high boiling point substances are encompassed into liquid crystals, the stability of the composition is improved, making all active components to fully exhibit their effects.

Branched alkyl type long-chain alkyltrimethylols of the formula (III) which are novel compounds take a form of thermotropic liquid crystals at room temperature. They have outstanding lubricity, can abundantly dissolve with almost all solvents, and disperse uniformly in water. Owing to these characteristics they are very useful compounds as a basic material, an emulsifier, and a lubricant for cosmetic composition.

Other features of the invention will become apparent in the course of the following description of the exemplary embodiments which are given for illustration of the invention and are not intended to be limiting thereof.

EXAMPLES

Reference Example [Preparation of aldehyde (II)]

Into a 3 l reaction vessel equipped with a thermometer, a dropping funnel, a hydrogen gas feed tube, and a stirrer were charged 1,000 ml of tetrahydrofuran, 27.2 g (0.25 mole) of 2,6-lutidine, and 5.0 g of 5% palladium-on-carbon (dry basis; product of Engerhard Industries Corp.). To the reaction vessel was dropwise added from a dropping funnel 76.2 g (0.25 mole) of isostearic acid chloride [prepared from isostearic acid (product of Emery Corp.]by a conventional method) over 1 hour at room temperature while stirring and passing hydrogen gas through the vessel. After the addition, the stirring was continued for a further 4 hours at room temperature while passing hydrogen gas through the vessel. The amount of hydrogen gas consumed in the reaction was about 2.7 mole.

Catalyst was removed from the reaction mixture by filtration and the solvent was evaporated under reduced pressure to obtain 68.1 g of isostearyl aldehyde (purity: 93%, yield: 94%).

Synthetic Example 1

Into a 3 l reaction vessel equipped with a thermometer, a reflux condenser, two dropping funnels, a nitrogen gas feed tube, and a stirrer were charged 100 g of (1.2 mole) of 35% aqueous formalin, 400 g of isopropanol, and 175 g of water. To the reaction vessel were dropwise added simultaneously from dropping funnels 190 g of 30% isopropanol solution of isostearyl aldehyde (isostearyl aldehyde: 0.2 mole) and 76.7 g (0.4 mole) of 20% aqueous solution of sodium hydroxide over a period of 6 hours at 40° C. while stirring and passing nitrogen gas through the vessel. After the addition, the stirring was continued for a further 2 hours at 40° C. to complete the reaction.

The reaction mixture was cooled to room temperature and the solvent was evaporated under reduced pressure to obtain 125 g of a crude product. To the crude product was added 300 g of toluene and the mixture was heated to dissolve. After washing the toluene solution twice with 100 g of hot water (60° C.), toluene was evaporated to obtain 63.1 g of crude trimethylolisoheptadecane. This crude material was purified by column chromatography on silica gel (eluant: hexane/methyl acetate) until thin-layer chromatography analysis gives a single spot to obtain 22.7 g of trimethylolisoheptadecane (yield: 34%). The product was a colorless transparent thermotropic crystals at room temperature.

IR (thin layer): $\gamma_{O-H}$(—CH$_2$OH)3400 cm$^{-1}$, $\gamma_{C-H}$ (stretching)

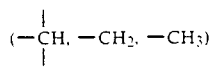

2860-2950 cm$^{-1}$, $\gamma_{C-H}$ (deformation)

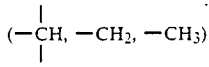

1380 cm$^{-1}$, 1470 cm$^{-1}$.

NMR (CDCl$_3$): δ(ppm) 3.64–3.85 (6H, broad, —CH$_2$OH) 3.22–3.48 (3H, broad, —CH$_2$OH) 1.12–1.43 (27H, broad, —CH$_2$,

0.78–1.04 (6H, broad, —CH$_3$)

Acid value: 0.06

Hydroxyl value: 499.1

Synthetic Example 2

Trimethylolisoheptadecane was prepared from isostearyl aldehyde prepared in Reference Example in the same manner as in Synthetic Example 1 except that 400 g of tetrahydrofuran was used instead of isopropanol. Through purification by column chromatography on silica gel (eluant: hexane/methyl acetate) 24.2 g (yield: 36%) of trimethylolisoheptadecane was produced which was colorless transparent thermotropic crystals at room temperature.

The results of analyses by thin layer chromatography, IR, and NMR were identical with the results obtained with trimethylolisoheptadecane prepared in Synthetic Example 1.

Test Example

Characteristics at room temperature and solubility with water of trimethylolisoheptadecane prepared in Synthetic Example 1 and conventionally known trimethylols were tested and compared. The results are shown in Table 1.

TABLE 1

| Tested Compounds | Characteristic (at room temperature) | Mutual solubility with water |
|---|---|---|
| Compound of this invention | | |
| trimethylolisoheptadecane | Thermotropic crystals | Homogeneously disperse |
| Comparative compounds | | |
| trimethylolpropane | Solid | Homogeneously disperse |
| trimethylolnonane | Solid | Solid/liquid separation |
| trimethylolheptadecane | Solid | Solid/liquid separation |
| trimethylolisoheptane | Viscous liquid | Liquid/liquid separation |

Example 1

Hair rinse compositions shown in Table 2 were prepared using the compound prepared in Synthetic Example 1. The rinsing performance of the compositions was evaluated.

(Preparation Method)

To hot water at a temperature of 70° C. the composition listed in Table 2 which was heated at 70° C. to melt was added and stirred. The mixture was cooled to room temperature with stirring to produce hair rinse compositions.

(Evaluation of Rinsing Performance)

Hair bundles, 15 cm long, weighing 20 g, were prepared. The hairs were those from Japanese women who had not received any beauty treatment such as cold perming and breaching in the past. Hair bundles were washed with a commercially available shampoo containing an anionic surface active agent as a major detergent component. After uniformly applying 2 g of hair rinse compositions shown in Table 2, the hair bundles were rinsed in a water stream for 30 seconds and dried with towel. Flexibility, smoothness, non-oiliness of these moistened hair bundles were evaluated. In the results shown in Table 2, those exhibiting excellent performance were rated AAA, those exhibiting good performance were rated BBB, those giving no effects were rated CCC, and those exhibiting bad performance were rated DDD.

Hair rinse compositions to which trimethylolisoheptadecane of the present invention was formulated had superior flexibility and smoothness and gave very slight oily sensation.

TABLE 2

| Components (wt %) | Invention Composition No. 1 | Comparative Compositions No. 1 | Comparative Compositions No. 2 | Comparative Compositions No. 3 |
|---|---|---|---|---|
| Trimethylolisoheptadecane' (Example 1) | 3.0 | — | — | — |
| Isostearyl alcohol | — | 3.0 | — | — |
| Isostearyl monoglyceride | — | — | 3.0 | — |
| Stearyltrimethylammonium chloride | 2.0 | 2.0 | 2.0 | 2.0 |
| Water | 95.0 | 95.0 | 95.0 | 98 |
| Sensory Evaluation | | | | |
| (1) Flexibility | BBB | DDD | CCC | BBB |
| (2) Smoothness | AAA | DDD | DDD | CCC |
| (3) Non-oiliness | AAA | CCC | BBB | BBB |

Example 2

Eighty percent (80%) of aqueous solutions of sample moisturizing agents were prepared. Each solution was placed in a Petri dish with a 30 mm diameter and allowed to stand in a P$_2$O$_5$ desiccator to measure the change in water content over time.

(Samples)

Compound 1 (the compound of of the present invention) Trimethylolisoheptadecane

Compound 2 (comparative compound) Propylene glycol

Compound 3 (comparative compound) Glycerine

The results are given in FIG. 1, which shows that the compound of the present invention exhibited a better moisture-retaining effect than conventional moisturizing agents.

Example 3

Hair rinse compositions shown in Table 3 were prepared and their rinsing performance were evaluated. The results are shown in Table 3.

(Treatment of Hairs)

Hair bundles, 15 cm long, weighing 20 g, were prepared. Hairs used were those taken from Japanese women who had not received any beauty treatment such as cold perming and bleaching in the past. For rinse-type hair cosmetics, 2 g of the cosmetic was uniformly applied to the hair bundles and the hairs were washed with running water for 30 seconds, and dried with towel, then with a dryer. For non-rinse-type hair cosmetics, a prescribed amount of the cosmetic was uniformly applied to the hair bundles and the hairs were air-dried. Hair bundles were subjected to sensory evaluations.

(Absorption of higher alcohol)

0.5 g of hairs treated as above was subjected to higher alcohol extraction with chloroform. The extract was concentrated, dissolved in a specified amount of chloroform containing an internal standard compound, and subjected to gas chromoatography to determine the amount of absorbed higher alcohol from the peak area.

(Sensory Evaluation)

The treated hair bundles were subjected to sensory evaluation by expert panelists. The evaluation was performed according to the following standard.

| | Smoothness |
|---|---|
| AAA | Excellent |
| BBB | Good |
| CCC | Cannot decide |
| DDD | Bad |
| | Non-oiliness |
| AAA | Imparts no oily sensation |
| BBB | Hardly imparts oily sensation |
| CCC | Imparts oily sensation (sticky) |
| DDD | Imparts strong oily sensation |
| | Moisturizing effect |
| AAA | Exhibits a good moisturizing effect |
| BBB | Exhibits a moisturizing effect |
| CCC | Cannot decide |

-continued

| DDD | Exhibits no moisturizing effect |
|---|---|

(State of compositions)

Hair rinse compositions were observed by a reflective microscope having a hot stage.
O: Forms a uniform liquid crystals
X: Does not form a uniform liquid crystals

TABLE 3

| | | Comparative Compositions | | | Invention Composition |
|---|---|---|---|---|---|
| Components (wt %) | | No. 4 | No. 5 | No. 6 | No. 2 |
| (1) | Stearyltrimethylammonium chloride | 2.0 | 2.0 | 2.0 | 2.0 |
| (2) | Cetyl alcohol | 3.0 | 3.0 | 3.0 | 3.0 |
| (3) | Trimethylolisoheptadecane | — | — | — | 1.5 |
| | Phytanetriol* | — | 1.5 | — | — |
| | Polyoxyethyleneoctyl-dodecylether (EO = 20) | — | — | 1.5 | — |
| (4) | Propylene glycol | 3.0 | 3.0 | 3.0 | 3.0 |
| (5) | Water | Balance | Balance | Balance | Balance |
| Effects imparted to hair | | | | | |
| Cetyl alcohol absorption (μmol/g hair) | | 0.9 | 1.5 | 1.1 | 2.2 |
| (Sensory Evaluation) | | | | | |
| Smoothness | | CCC | BBB | DDD | BBB |
| Non-oiliness | | CCC | DDD | BBB | BBB |
| Moistened sensation | | DDD | CCC | DDD | AAA |
| State of compositions | | | | | |
| (at room temperature) | | X | X | X | O |

*Trade name: 3-7-11-tetramethyl-1,2,3-trihydroxy-hexadecane of the following formula, produced by Kuraray Co., Ltd.

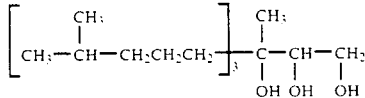

Example 4

Hair rinse compositions shown in Table 4 were prepared and their rinsing performances were evaluated. The results are shown in Table 4.

(Method of preparation)

To the mixture of components (8)–(10) and (12) heated to 70° C., the mixture of components (1)–(7) heated to the same temperature to dissolution was added and stirred to emulsify. The emulsion was allowed to cool to 45° C. while stirring and component (11) was added with stirring thus obtaining hair rinse compositions.

All hair rinse compositions exhibited good hair rinse performance and possessed superior stability. Sensory evaluation was peformed in the same manner as in Example 3.

(Storage stability)

Samples were placed in a 100 ml transparent glass container. After having been stored, the samples were observed by the naked eye. The evaluation was rated according to the following criterion.
O: The whole composition was uniform without any abnormality such as dispersion or coagulation.
X: The composition was not uniform with dispersion or coagulation.

TABLE 4

| Components (wt %) | Invention Compositions | | | |
|---|---|---|---|---|
| | No. 3 | No. 4 | No. 5 | No. 6 |
| (1) Dialkyldimethylammonium chloride** | 1.0 | 1.0 | — | 0.5 |
| 2-dodecylhexadecyl-trimethylammonium chloride | — | — | 1.0 | 0.5 |
| Cetostearyltrimethyl-ammonium chloride | 1.0 | 1.0 | 1.0 | 1.0 |
| (2) Trimethylolisoheptadecane | 1.0 | 1.0 | 2.0 | 0.5 |
| Trimethyloltridecane | — | 0.5 | 1.0 | — |
| (3) Cetostearyl alcohol | 3.0 | 2.5 | 2.0 | 3.0 |
| (4) Polyoxyethylenecetyl ether (EO = 5) | 0.2 | 0.2 | 0.2 | 0.3 |
| (5) Liquid paraffin | 0.5 | 0.3 | 0.3 | 0.3 |
| (6) Dimethylpolysiloxane (1,000 cs) | 0.5 | 0.5 | 0.5 | 0.5 |
| (7) Propylene glycol | 3.0 | 3.0 | 3.0 | 3.0 |
| (8) Hydroxyethyl cellulose | 0.3 | 0.3 | — | — |
| Hydroxymethyl cellulose | — | — | 0.3 | 0.3 |
| (9) Preservative | appropriate amount | appropriate amount | appropriate amount | appropriate amount |
| (10) Pigment | small amount | small amount | small amount | small amount |
| (11) Perfume | small amount | small amount | small amount | small amount |
| (12) Purified water | balance | balance | balance | balance |
| (Sensory Evaluation) | | | | |
| Smoothness | AAA | AAA | AAA | AAA |
| Non-oiliness | AAA | AAA | AAA | AAA |
| Moistened sensation | AAA | AAA | AAA | AAA |
| (Storage Stability) | | | | |
| At room temperature (3 months) | 0 | 0 | 0 | 0 |
| At 40° C. (3 months) | 0 | 0 | 0 | 0 |

**A salt of branched quaternary ammonium with a 20% branch proportion. The compound is derived from commercially available oxo alcohol having 12-15 carbon atoms [An equivalent amount mixture of Dovanol 23 and Dovanol 45 (both are trade names; manufactured by Mitsubishi Petrochemical Co., Ltd.)].

Example 5

Hair treatment composition (Invention Composition No. 7)

| | | |
|---|---|---|
| (1) 2-dodecylhexadecyltrimethyl-ammonium chloride | 1.5 wt % |
| (2) Stearyltrimethylammonium chloride | 1.0 |
| (3) Dimethylpolysiloxane (500 cs) | 1.0 |
| (4) Cetostearyl alcohol | 3.0 |
| (5) Trimethylolisoheptadecane | 3.0 |
| (6) Liquid paraffin | 3.0 |
| (7) Polypeptide (collagen hydrolyzate) | 5.0 |
| (8) Hydroxyethyl cellulose (1% aqueous solution; viscosity: 8,000 cp) | 0.5 |
| (9) Polyoxyethyleneoleyl ether (EO = 5) | 0.5 |
| (10) Methyl paraben | 0.2 |
| (11) Perfume | 0.4 |
| (12) Water | Balance |
| Total | 100.0 |

A hair treatment composition has superior smoothness, flexibility, an non-oiliness, and yet gave a soft, moistened, and comfortable sensation.

Example 6

Hair cream composition (Invention Composition No. 8)

| | |
|---|---|
| (1) di-2-hexyldecyldimethylammonium chloride | 2.0 wt % |
| (2) Cetyltrimethylammonium chloride | 1.0 |
| (3) Modified silicone aqueous suspension*** | 2.0 |
| (4) Trimethylolisoheptadecane | 1.0 |
| (5) Cetyl alcohol | 5.0 |
| (6) Dipropylene glycol | 6.0 |
| (7) Glycerine | 10.0 |
| (8) Liquid paraffin | 3.0 |
| (9) Perfume | 0.4 |
| (12) Water | Balance |
| Total | 100.0 |

***SM 8702C (trade name, product of Toray Silicone Co., Ltd. containing 40% a modified-silicone polymer A hair cream has superior smoothness, flexibility, and non-oiliness, and yet gave a soft, moistened, and comfortable sensation.

Example 7

Style lotion composition (Invention Composition No. 9)

| | |
|---|---|
| (1) 2-Dodecylhexadecyltrimethyl-ammonium chloride | 0.5 wt % |
| (2) Trimethylolisoheptadecane | 0.2 |
| (3) Modified silicone aqueous suspension*** | 1.0 |
| (4) Methacrylate polymer**** | 1.0 |
| (5) Polyethylene glycol | 1.0 |
| (6) Ethanol | 20.0 |
| (7) Perfume | 0.3 |
| (12) Water | Balance |
| Total | 100.0 |

***The same as in Example 5.
****Yukaformer, product of Mitsubishi Petrochemical Co., Ltd.

A hair set composition was prepared, which gave a good feeling upon use and a superior hair style retaining characteristic.

Example 8

Conditioning mousse composition (Invention Composition No. 10)

| | | |
|---|---|---|
| (1) | Dialkyldimethylammonium chloride** | 0.5 wt % |
| (2) | Methylphenylpolysiloxane (300 cs) | 1.0 |
| (3) | Isododecyl myristate | 1.0 |
| (4) | 3-methyl-1,3-butanediol | 1.0 |
| (5) | Glycerine | 2.5 |
| (6) | Liquid paraffin | 2.5 |
| (7) | Trimethylolisoheptadecane | 0.2 |
| (8) | 95% Ethanol | 5.0 |
| (9) | Methyl paraben | 0.1 |
| (10) | Perfume | 0.1 |
| (11) | Propellant (LPG) | 10.0 |
| (12) | Water | Balance |
| | Total | 100.0 |

**The foot note of Table 4 applies.

A conditioning mousse composition which imparted good sensation upon use was prepared.

Example 9

Cream (Invention Composition No. 11)

| | |
|---|---|
| Oil phase components: | |
| Cetanol | 2.0(%) |
| Stearic acid | 3.0 |
| Trimethylolisoheptadecane | 3.0 |
| Trimethyloltridecane | 2.0 |
| Lipid isostearic acid cholesteryl (ester) | 8.0 |
| Monolaurylglycerine | 2.0 |
| Polyoxyethylene sorbitanemonolauric acid ester (EO = 20) | 2.0 |
| Water phase components: | |
| Dipropylene glycol | 10.0 |
| 1,3-butylene glycol | 5.0 |
| Ethyl paraben | 0.1 |
| Methyl paraben | 0.2 |
| Perfume | 0.1 |
| Water | Balance of both oil and water components |

The cream gave good sensation upon use and an excellent moisture-retaining effect.

Example 10

Emulsion (Invention Composition No. 12)

| | |
|---|---|
| Oil phase components: | |
| Cetanol | 0.5(%) |
| Petrolatum | 1.0 |
| Trimethylolisoheptadecane | 10.0 |
| Polyoxyethylenemonooleic acid ester (EO = 10) | 2.0 |
| Stearic acid | 2.0 |
| Water phase components: | |
| 1,3-butylene glycol | 3.0 |
| Dipropylene glycol | 6.0 |
| Triethanolamine | 1.0 |
| Ethyl paraben | 0.1 |
| Methyl paraben | 0.2 |
| Perfume | 0.1 |
| Water | 74.1 |
| Total | 100.0 |

The emulsion exhibited an excellent moisture-retaining effect.

Example 11

Cosmetic base (Invention Composition No. 13)

| | |
|---|---|
| Glycerine | 15(%) |
| Polyoxyethylenoctyldodecyl ether (EO = 20) | 10 |
| Trimethylolisoheptadecane | 10 |
| Squalane | 50 |
| Water | Balance |
| Total | 100 |

All above components were subjected to procedures comprising dissolution with heating, blending, and cooling to prepare a single phase cosmetic base. Various oil-soluble compounds can be blended with this base material to produce cosmetic products.

Example 12

Emulsion-type foundation (Invention Composition No. 14)

| | |
|---|---|
| Oil phase components: | |
| Stearic acid | 5.0(%) |
| Cetostearyl alcohol | 1.0 |
| Trimethyloltridecane | 0.5 |
| Trimethylolisoheptadecane | 6.0 |
| Lipid (isostearic acid choresteryl ester) | 6.0 |
| Monolauryl glycerine | 2.0 |
| Propylene glycol monolauric acid | 3.0 |
| Water phase components: | |
| Glycerine | 10.0 |
| Triethanolamine | 1.2 |
| Ethyl paraben | 0.1 |
| Methyl paraben | 0.1 |
| Perfume | 0.1 |
| Purified water | Balance |
| Powdery components: | |
| Titanium oxide | 8.0 |
| Talc | 4.0 |
| Iron oxide | 0.5 |
| Total | 100.0 |

The emulsion gave good sensation upon use and exhibited an excellent moisture-retaining effect.

Example 13

Lipstick

| | |
|---|---|
| Microcrystalline wax | 6.0(%) |
| Candelilla wax | 3.0 |
| Diisostearic acid glycerine ester | 5.0 |
| Trimethylolisoheptadecane | 10.0 |
| Lipid (Cerebroside; product of Sedary Research Laboratories Inc.) | 2.0 |
| Jojova oil | 6.0 |
| Olive oil | Balance |
| Lanolin | 10.0 |
| Pigment | 7.0 |
| Perfume | 0.1 |
| Total | 100.0 |

The lipstick gave good sensation upon use and exhibited an excellent moisture-retaining effect.

Example 14

Shampoo (Invention Composition No. 16)

| | |
|---|---|
| Triethanolamine lauryl sulfate | 20(%) |
| Lauric acid diethanolamide | 3 |
| Trimethylolisoheptadecane | 2 |
| Perfume | 0.3 |
| Pigment | Small amount |
| Water | Balance |
| Total | 100.0 |

The shampoo gave good sensation upon use and exhibited an excellent moisture-retaining effect.

Example 15

Shampoo (Invention Composition No. 17)

| | |
|---|---|
| N-lauroyl-N'-carboxymethyl-N'-(2-hydroxyethyl)ethylenediamine triethanolamine | 12(%) |
| Disodium polyoxyethylenelauryl-sulfosuccinate | 5 |
| Lauric acid diethanolamide | 3 |
| Cationic polymer (Marcoat 100, product of Merck Co.) | 0.2 |
| Trimethylolisoheptadecane | 0.2 |
| Preservative | 0.1 |
| Perfume/pigment | Suitable amount |
| Water | Balance |
| Total | 100.0 |

The shampoo gave very weak stimulation to the skin and exhibited an excellent conditioning effect.

Example 16

Cleansing cream (Invention Composition No. 18)

| | |
|---|---|
| Sorbitol | 10(%) |
| Polyoxyethylenoctyldodecyl ether (EO = 25) | 15 |
| Trimethylolisoheptadecane | 60 |
| Glycerine | 5 |
| Dibutylhydroxytoluene | 0.1 |
| Methyl paraben | 0.1 |
| Perfume | 0.1 |
| Water | Balance |
| Total | 100.0 |

The cleansing cream of the present invention exhibited excellent stability and gave superior dirt removing performance.

Example 17

Soap (Invention Composition No. 19)

| | |
|---|---|
| Beef tallow/coconut oil soap | 97.3(%) |
| Trimethylolnonane | 0.5 |
| Trimethylolisoheptadecane | 0.5 |
| Perfume | 1.5 |
| Coloring agent | 0.2 |
| Total | 100.0 |

The soap of the present invention gave favorable feeling upon use and provided an effect of suppressing roughened sensation.

Example 18

Body shampoo (Invention Composition No. 20)

| | |
|---|---|
| Lauryl phosphate | 8.0(%) |
| Lauric acid | 3.2 |
| Triethanolamine | 10.0 |
| Glycerine | 3.0 |
| Trimethylolisoheptadecane | 2.0 |
| Dibutylhydroxytoluene | 0.1 |
| Hydroxyethyl cellulose (1% aqueous solution, 8,000 cp) | 0.5 |
| Ethanol | 3.0 |
| Perfume | 0.5 |
| Water | Balance |
| Total | 100.0 |

The body shampoo of the present invention gave favorable feeling upon use and provided an effect of suppressing roughened sensation.

Obviously, numerous modifications and variations of the present invention are possible in light of the above teachings. It is therefore to be understood that within the scope of the appended claims, the invention may be practiced otherwise than as specifically described herein.

What is claimed is:

1. A cosmetic composition, comprising:
a branched, long-chain alkyltrimethylol of the formula:

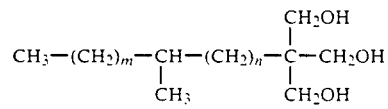

wherein m and n are independently 0 or an integer of 1–19 provided that the sum of m+n is 7–19, in combination with at least one surfactant and other additives selected from the group consisting of higher alcohols, lanolin derivatives, silicone derivatives, higher fatty acid esters of higher alcohols, higher fatty acids, natural oils and fats, medicinal ingredients, preservatives, viscosity increasing agents, coloring agents, UV absorbers, astringents, moisture-retaining agents, water and perfumes useful in cosmetic formulations.

2. The composition of claim 1, wherein said surfactant is a cationic, anionic, amphoteric or nonionic surfactant.

3. The cosmetic composition of claim 1, wherein the surfactant is present in the composition in an amount ranging from 0.01–30% by weight.

4. A branched alkyl long-chain alkyltrimethylol of formula (III):

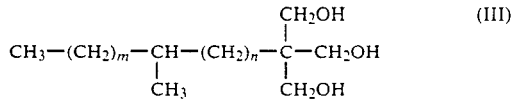

wherein m and n are each independently 0 or an integer of 1–19, provided that the sum m+n is 7–19.

5. The long-chain alkyltrimethylol of claim 4, wherein the sum m+n is 11–15.

6. A compound of the formula:

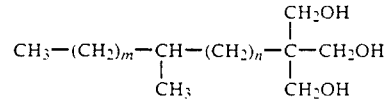

wherein m and n are each independently 0 or an integer of 1–19, provided that the sum m+n is 13.

* * * * *